United States Patent
Sakakura et al.

(10) Patent No.: US 8,368,397 B2
(45) Date of Patent: Feb. 5, 2013

(54) MAGNETIC RESONANCE IMAGING APPARATUS AND MAGNETIC RESONANCE IMAGING METHOD

(75) Inventors: Yoshitomo Sakakura, Nasushiobara (JP); Hiroshi Kusahara, Nasushiobara (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 310 days.

(21) Appl. No.: 12/521,804

(22) PCT Filed: Feb. 13, 2009

(86) PCT No.: PCT/JP2009/052396
§ 371 (c)(1),
(2), (4) Date: Oct. 12, 2010

(87) PCT Pub. No.: WO2009/107492
PCT Pub. Date: Sep. 3, 2009

(65) Prior Publication Data
US 2011/0095760 A1    Apr. 28, 2011

(30) Foreign Application Priority Data
Feb. 29, 2008  (JP) ................... 2008-050837

(51) Int. Cl.
*G01V 3/00*   (2006.01)
(52) U.S. Cl. ........................... 324/307; 324/309
(58) Field of Classification Search .......... 324/300–322; 600/407–445; 382/131
See application file for complete search history.

(56) References Cited

U.S. PATENT DOCUMENTS

| | | | |
|---|---|---|---|
| 4,791,369 A | 12/1988 | Yamamoto et al. | |
| 4,982,159 A | 1/1991 | Hoshino | |

(Continued)

FOREIGN PATENT DOCUMENTS

| | | |
|---|---|---|
| JP | 63-19138 | 1/1988 |
| JP | 63-21048 | 1/1988 |

(Continued)

OTHER PUBLICATIONS

English translation of International Preliminary Report on Patentability dated Oct. 12, 2010 in PCT/JP2009/052396, including Written Opinion of the International Searching Authority.

(Continued)

*Primary Examiner* — Brij Shrivastav
(74) *Attorney, Agent, or Firm* — Nixon & Vanderhye PC

(57) ABSTRACT

A magnetic resonance imaging apparatus has a storage unit and a processing unit. The storage unit stores correction data of a position coordinate, in which the position coordinate in the reconstruction FOV is caused to correspond to a position coordinate in a display FOV included in the reconstruction FOV based on an intensity of a gradient magnetic field. If both of a first position coordinate and a second position coordinate, which is further from the center of the reconstruction FOV, correspond to same position coordinate in the display FOV, the correction data is data for causing only the first position coordinate to correspond to the position coordinate in the display FOV. The processing unit corrects a reconstructed image based on the correction data and obtains an image of the display FOV.

7 Claims, 6 Drawing Sheets

U.S. PATENT DOCUMENTS

| | | | |
|---|---|---|---|
| 6,707,300 B2 * | 3/2004 | Polzin et al. | 324/309 |
| 6,894,494 B2 * | 5/2005 | Stergiopoulos et al. | 324/309 |
| 6,967,479 B2 * | 11/2005 | Polzin et al. | 324/318 |
| 7,843,194 B2 * | 11/2010 | Kassai | 324/309 |
| 8,217,652 B2 * | 7/2012 | Dannels | 324/309 |
| 2004/0092809 A1 * | 5/2004 | DeCharms | 600/410 |
| 2007/0191704 A1 * | 8/2007 | DeCharms | 600/411 |
| 2009/0318794 A1 * | 12/2009 | DeCharms | 600/410 |
| 2011/0044524 A1 * | 2/2011 | Wang et al. | 382/131 |

FOREIGN PATENT DOCUMENTS

| | | |
|---|---|---|
| JP | 63-216556 | 9/1988 |
| JP | 2007-325665 | 12/2007 |

OTHER PUBLICATIONS

International Search Report for PCT/JP2009/052396 mailed Mar. 10, 2009.

* cited by examiner

MAGNETIC RESONANCE IMAGING APPARATUS AND MAGNETIC RESONANCE IMAGING METHOD

This application is the U.S. national phase of International Application No. PCT/JP2009/052396 filed 13 Feb. 2009 which designated the U.S. and claims priority to Japanese Patent Application No. 2008-050837 filed 29 Feb. 2008, the entire contents of each of which are hereby incorporated by reference.

BACKGROUND

1. Technical Field

The present invention relates to a magnetic resonance imaging apparatus and a magnetic resonance imaging method for providing a good diagnostic image from which an artifact caused by an uneven static magnetic field and a nonlinear gradient magnetic field is removed.

2. Background Art

An MRI apparatus has a static field generation magnet formed about an axial center in an advancing/retreating direction of a table-top, a shim coil formed inward of the static field generation magnet about the axial center in the advancing/retreating direction of the table-top, gradient coils formed inward of the shim coil about the axial center in the advancing/retreating direction of the table-top, and a liner set on inner side of the gradient coils about the axial center in the advancing/retreating direction of the table-top, and forming a bore through which the table-top advances and retreats. During imaging, the MRI apparatus generates a static magnetic field in the bore formed by the liner, and the gradient coils form gradient magnetic fields in X-, Y-, and Z-directions in an imaging area of a patient set in the bore. Further, the MRI apparatus causes a nuclear spin in the patient to magnetically resonate by transmitting an RF signal from an RF (high-frequency) coil provided with the MRI apparatus, and reconstructs an image in a reconstruction FOV (field of view) in the patient making use of an NMR (nuclear magnetic resonance) signal generated by an excitation.

However, an artifact is generated to a reconstructed image due to an uneven static magnetic field and nonlinear gradient magnetic fields. To cope with the above problem, there is disclosed a technology for correcting an artifact on a reconstructed image caused by an uneven static magnetic field (refer to, for example, Japanese Patent Application Publication 2006-61235).

In contrast, to correct an artifact on a reconstructed image caused by the intensities of gradient magnetic fields with the nonlinearity, there is known a technology for previously providing a position coordinate correction table for causing the distribution of the intensities of actual gradient magnetic fields with the nonlinearity to agree with the distribution of the linear intensities of virtual gradient magnetic fields and correcting a reconstructed image using the correction table. Conventionally, since a display FOV (in a displayed image) that is a display area of a display image is small regardless whether a bore diameter is relatively narrow (for example, 600 mm) or relatively wide (for example, 700 mm), an artifact is corrected well even if a reconstruction FOV (in the patient) approximately agrees with the display FOV (in the image).

However, when the bore diameter is relatively large and the display FOV is relatively large, the reconstruction FOV must be widened more than the display FOV to appropriately correct an artifact generated on a side away from the center of a magnetic field (center of the reconstruction FOV) in the display FOV. This is because since the intensities of the actual gradient magnetic field become more nonlinear as they are away from the center of the magnetic field, the information of position coordinates on a side away from the center of the magnetic field in the display FOV must be supplemented by the information of position coordinates externally of the display FOV.

However, when the reconstruction FOV is widened, a part, in which the distribution curve of the intensities of the gradient magnetic fields is shown by a two-value function, appears in the reconstruction FOV. In this case, according to the conventional technology, since a plurality of position coordinates in the intensities of actual gradient magnetic fields correspond to one position coordinate in the display FOV in the intensities of virtual gradient magnetic fields, an appropriate correction table cannot be generated. In particular, since a bore diameter and a display FOV tend to enlarge now, it is desired to appropriately correct a reconstructed image because it is expected that an artifact is liable to be generated on a reconstructed image. When an artifact exists on a display image, it may be an obstacle for diagnosis.

BRIEF SUMMARY

A purpose of the present exemplary embodiment, which was made in view of the above circumstances, is to provide a magnetic resonance imaging apparatus and a magnetic resonance imaging method capable of generating and displaying a good diagnostic image from which an artifact is removed even if a relatively wide display FOV is set.

To solve the problems described above, a magnetic resonance imaging apparatus according to the present exemplary embodiment has: a static field generation magnet configured to generate a static magnetic field; a gradient coil configured to apply gradient magnetic field, which is superimposed on the static magnetic field, to an object; an RF coil configured to receive a magnetic resonance signal generated by the object; an image reconstructing unit configured to generate a reconstructed image in a reconstruction FOV (field of view) of the object based on the magnetic resonance signal; a correction data storage unit configured to store correction data of a position coordinate, in which the position coordinate in the reconstruction FOV is caused to correspond to a position coordinate in a display FOV included in the reconstruction FOV based on an intensity of the gradient magnetic field, wherein if both of a first position coordinate, which is near from a center of the reconstruction FOV, in the reconstruction FOV and a second position coordinate, which is far from the center, in the reconstruction FOV correspond to same position coordinate in the display FOV, the correction data is data for causing only the first position coordinate to correspond to the position coordinate in the display FOV; and an image processing unit configured to correct the reconstructed image based on the correction data, and to obtain an image of the display FOV.

To solve the problems described above, a magnetic resonance imaging method according to the present exemplary embodiment has: a step of receiving a magnetic resonance signal generated from an object in a state that a gradient magnetic field superimposed on a static magnetic field is applied to the object, and generating a reconstructed image in a reconstruction FOV of the object based on the magnetic resonance signal; and a step of correcting the reconstructed image based on correction data of a position coordinate, in which the position coordinate in the reconstruction FOV is caused to correspond to a position coordinate in a display FOV included in the reconstruction FOV based on an intensity of the gradient magnetic field, and which causes only a first position coordinate to correspond to the position coordinate in the display FOV if both of the first position coordinate, which is near from a center of the reconstruction FOV, in the reconstruction FOV and a second position coordinate, which is far from the center, in the reconstruction FOV correspond to same position coordinate in the display FOV, and obtaining an image of the display FOV.

DETAILED DESCRIPTION OF EXEMPLARY EMBODIMENTS

An embodiment of an MRI apparatus and an MRI method according to the present invention will be explained referring to the accompanying drawings.

Figure 1:
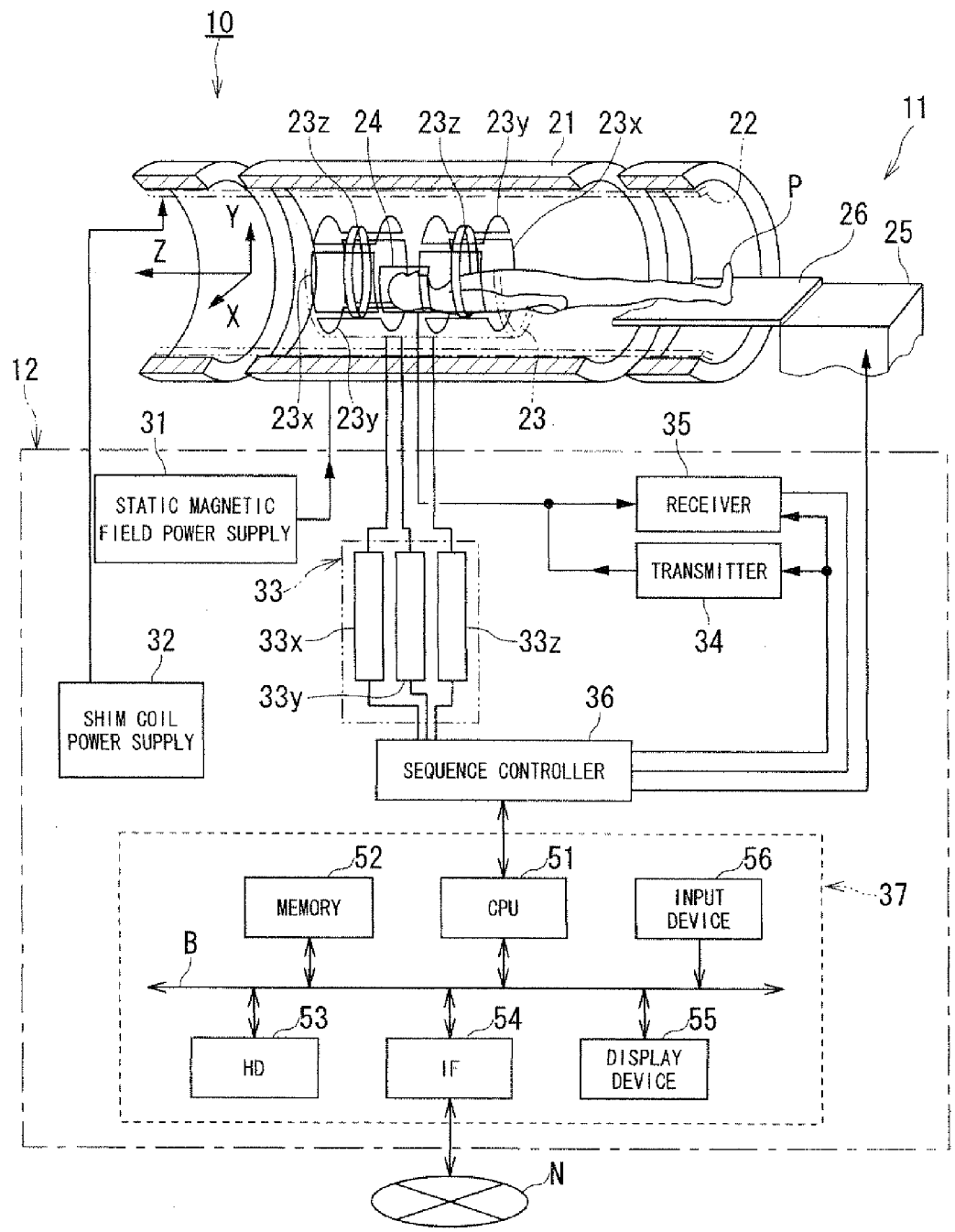
FIG. 1 is a schematic view showing a hardware arrangement of an MRI apparatus of an embodiment.

FIG. 1 is a schematic view showing a hardware arrangement of the MRI apparatus of the present embodiment.

FIG. 1 shows the MRI apparatus 10 of the embodiment. The MRI apparatus 10 is mainly composed of an imaging system 11 and a control system 12.

The imaging system 11 of the MRI apparatus 10 has a gantry (not shown) for accommodating a static field generation magnet (main field magnet) 21, a shim coil 22, which is formed internally of the static field generation magnet 21 coaxially therewith, and a gradient coil unit 23 formed internally of the static field generation magnet 21. Further, the imaging system 11 is provided with an RF coil 24 for transmitting an RF signal having a Larmor frequency (resonance frequency) and a bed mechanism 25 for advancing and retreating a patient P into and from the gantry.

In contrast, the control system 12 of the MRI apparatus 10 has a static magnetic field power supply 31, a shim coil power supply 32, a gradient power supply 33, a transmitter 34, a receiver 35, a sequence controller (sequencer) 36, and an image processing device 37.

If the static field generation magnet 21 is excited, the static field generation magnet 21 is connected to the static magnetic field power supply 31. A static magnetic field is formed in an imaging area (FOV: field of view) by a current supplied from the static magnetic field power supply 31.

The shim coil 22 is connected to the shim coil power supply 32, is supplied with a current therefrom, and makes the static magnetic field uniform.

The gradient coil unit 23 is composed of an X-axis gradient coil 23x, a Y-axis gradient coil 23y, and a Z-axis gradient magnetic field coil 23z. Further, a table-top 26 of the bed mechanism 25 is disposed inside of the gradient coil unit 23, and the patient P is placed thereon. The table-top 26 is moved by the bed mechanism 25.

Further, the gradient coil unit 23 is connected to the gradient power supply 33. The X-axis gradient coil 23x, the Y-axis gradient coil 23y, and the Z-axis gradient coil 23z of the gradient coil unit 23 are connected to an X-axis gradient power supply 33x, a Y-axis gradient power supply 33y, and a Z-axis gradient power supply 33z of the gradient power supply 33, respectively. Then, a gradient magnetic field Gx in an X-direction, a gradient magnetic field Gy in a Y-direction, and a gradient magnetic field Gz in a Z-direction are formed in the imaging area, respectively by currents supplied from the X-axis gradient power supply 33x, the Y-axis gradient power supply 33y, and the Z-axis gradient power supply 33z to the X-axis gradient coil 23x, the Y-axis gradient coil 23y, and the Z-axis gradient coil 23z, respectively.

The RF coil 24 is composed of a multi coil and connected to the transmitter 34 and the receiver 35. The RF coil 24 has a function for receiving an RF signal from the transmitter 34 and transmitting an RF magnetic field pulse to an imaging region (object) of the patient P and a function for receiving an NMR signal generated by the excitation of a nuclear spin in the imaging region caused by the RF signal and supplying the NMR signal to the receiver 35. A transmission/reception system of the RF coil 24 is divided into a system in which one coil is used as both a transmission coil and a reception coil and a system in which different coils are used as a transmission coil and a reception coil. Note that, although the MRI apparatus 10 is provided with the RF coil 24, FIG. 1 exemplifies only a coil used for a head region as an example of the RF coil 24.

In contrast, the sequence controller 36 of the control system 12 is connected to the bed mechanism 25, the gradient power supply 33, the transmitter 34, and the receiver 35. The sequence controller 36 has a not shown processor, for example, a CPU (central processing unit) and a memory and stores control information necessary to drive the bed mechanism 25, the gradient power supply 33, the transmitter 34, and the receiver 35, for example, sequence data, in which operation control information such as the intensity, the application time, the timing of application, and the like of a pulse current to be applied to the gradient power supply 33, is described.

The sequence controller 36 causes the table-top 26 to advance to and retreat from the gantry in the Z-direction by driving the bed mechanism 25 according a predetermined sequence data stored thereto. Further, the sequence controller 36 generates the X-axis gradient magnetic field Gx, the Y-axis gradient magnetic field Gy, Z-axis gradient magnetic field Gz, and the RF signal in the gantry by driving the gradient power supply 33, the transmitter 34, and the receiver 35 according to a predetermined sequence stored thereto.

The transmitter 34 applies the RF signal to the RF coil 24 based on the control information received from the sequence controller 36. In contrast, the receiver 35 performs a required signal process for the NMR signal received from the RF coil 24, as well performs an A/D (analog to digital) conversion so that raw data as a digitized NMR signal is generated from the receiver 35. Further, the receiver 35 applies the raw data generated thereby to the sequence controller 36. The sequence controller 36 receives the raw data from the receiver 35 and applies it to the image processing device 37.

The image processing device 37 is composed of basic hardware as a computer such as a CPU 51 as a processor, a memory 52, an HD (hard disk) 53, an IF (interface) 54, a display device 55, an input device 56, and the like. The CPU 51 is mutually connected to the respective hardware components 52, 53, 54, 55, and 56 that constitute the image processing device 37 through a bus B as a common signal transmission path. Further, since the image processing device 37 is connected to a network N such as a hospital LAN (local area network) and the like through the IF 54 so that the image processing device 37 can perform a mutual communication, it can obtain past images to be described later from a not shown image management device (server) on the network N.

Note that the image processing device 37 may be provided with a drive for reading various application programs and data from a medium that stores the various application programs and the data.

The CPU 51 is a controller composed of an integrated circuit (LSI) arranged such that electronic circuits composed of semiconductors are enclosed in a package having a plurality of terminals. The CPU 51 has a function for executing a program stored in the memory 52. Further, the CPU 51 has a function for loading a program, which is stored in the HD 53, and a program, which is transferred from the network N, received by the IF 54, and installed on the HD 53, on the memory 52 and executing the program.

The memory 52 is a storage device also acting as a ROM (read only memory) and a RAM (random access memory), and the like. The memory 52 has a function for storing BIOS (basic input/output system), IPL (initial program loading), and images and temporarily storing a work memory and data of the CPU 51.

The HD 53 is a storage device composed of a metal disk on which a magnetic substance is coated or vapor deposited and incorporated in a read-out device (not shown) so that it cannot be dismounted therefrom. The HD 53 has a function for storing the programs (including OS (operating system) and the like in addition to application programs) which are installed on the image processing device 37 and images. Further, it is also possible to cause OS to provide GUI (graphical user interface) which permits an operator to perform basic operations through the input device 56 by frequently using graphics to show various kinds of information to the operator.

The IF 54 is composed of a connector arranged in accordance with a parallel connection specification and a serial connection specification. The IF 54 has a function which performs a communication control in accordance with respective standards and can be mutually connected to the network N. The MRI apparatus 10 is connected to an image reader, a medical image data server, and the like, which are not shown, through the IF 54 and the network N so that it can communicate therewith.

The display device 55 is composed of an image synthesization circuit, a D/A (digital to analog) conversion circuit, and a two-dimensional monitor, and the like. The display device 55 has a function for displaying an MRI image through the monitor.

The input device 56 is composed of a keyboard, a mouse, and the like which can be operated by a technician and the like. The input device 56 has a function for transmitting an input signal according to an operation to the CPU 51.

Figure 2:
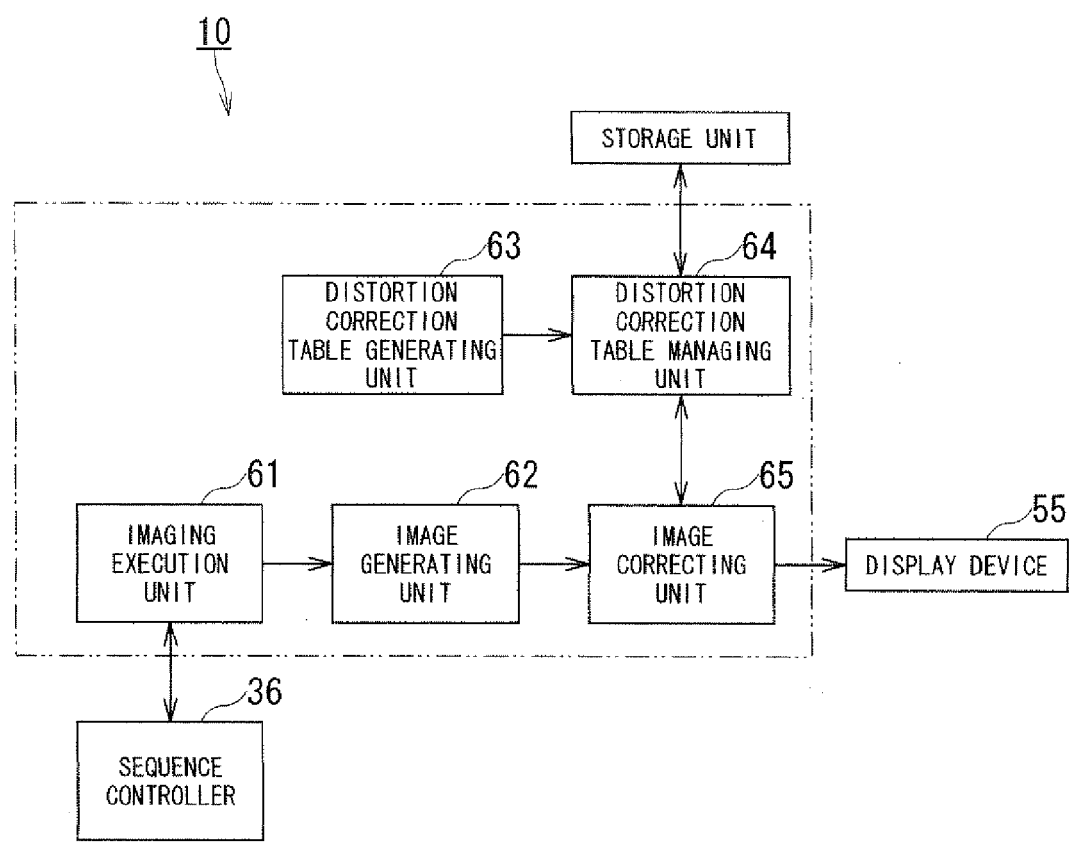
FIG. 2 is a block diagram showing a function of the MRI apparatus of the embodiment.

FIG. 2 is a block diagram showing a function of the MRI apparatus of the embodiment.

If the CPU 51 or the CPU of the sequence controller 36 shown in FIG. 1 executes a program, the MRI apparatus 10 has functions as an imaging execution unit 61, an image generating unit 62, a distortion correction table generating unit 63, a distortion correction table managing unit 64, and an image correcting unit 65 as shown in FIG. 2. Note that, although a case, in which the respective units 61 to 65 of the MRI apparatus 10 act as software, will be explained, the respective units 61 to 65 may be entirely or partly disposed to the MRI apparatus 10 as hardware.

Although the intensities of the Z-axis gradient magnetic field formed by the Z-axis gradient coil 23z will be explained below, it is assumed that this is also applied to the respective intensities of the gradient magnetic fields formed by the X-axis gradient coil 23x and the Y-axis gradient coil 23y likewise.

The imaging execution unit 61 has a function for picking up an MR image of the patient P by controlling the sequence controller 36 according to the pulse sequence of imaging methods such as an SE (spin echo) method, an FE (field echo) method, and the like. Further, the imaging execution unit 61 has a function for disposing digital raw data, output from the sequence controller 36, as k-space data in a k-space which is formed to a k-space database (not shown).

The image generating unit 62 has a function for applying predetermined image reconstruction processes such as a two- or three-dimensional Fourier conversion process, a maximum value projection process, and the like to the k-space data obtained by the imaging execution unit 61, and generating a reconstructed image in a reconstruction FOV in an actual Z-axis gradient magnetic field with a nonlinearity.

The distortion correction table generating unit 63 generates a temporary distortion correction table such that a Z-component, which is included in a position coordinate in the reconstruction FOV in a distribution of intensities of the actual Z-axis gradient magnetic field with the nonlinearity (shown in FIG. 5), becomes a 7-component, which is included in a position coordinate in the display FOV in the distribution of the intensities of a virtual Z-axis gradient magnetic field (shown in FIG. 4) to correct an artifact caused by the intensities of the actual Z-axis gradient magnetic field with the nonlinearity on the reconstructed image. However, if a bore diameter is relatively large (for example, 700 mm or more) as well as the display FOV is relatively large, a plurality of Z-components in the reconstruction FOV in the distribution of the intensities of the actual Z-axis gradient magnetic field correspond to one Z-component in the display FOV in the distribution of the intensities of the virtual Z-axis gradient magnetic field.

Figure 3:
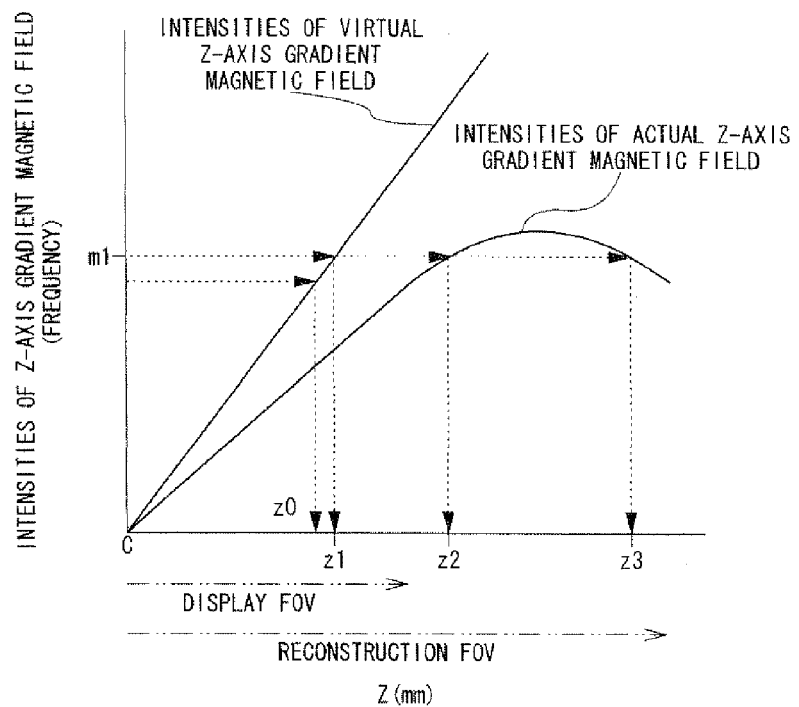
FIG. 3 is a view showing an example of the relation between the intensities (frequencies) of a Z-axis gradient magnetic field and a Z-component.

FIG. 3 is a view showing an example of the relation between the intensities (and thus Larmor frequencies) of the Z-axis gradient magnetic field and the Z-component.

As shown in FIG. 3, in the intensities of the virtual Z-axis gradient magnetic field in required X- and Y-components, a Z-component linearly rises from the center of the magnetic field (center of the reconstruction FOV) C toward an edge side. However, in the intensities of the actual Z-axis gradient magnetic field formed by the Z-axis gradient coil 23z, a Z-component is shown by a two-value function which gradually rises and falls from the center C of the magnetic field toward the edge side. If the range of the display FOV in the virtual Z-axis gradient magnetic field is set smaller than the Z-component $z0$, since one Z-component in the reconstruction FOV corresponds to one Z-component in the display FOV, distortion can be sufficiently corrected by the temporary distortion correction table generated by the distortion correction table generating unit 63.

However, if the range of the display FOV in the virtual Z-axis gradient magnetic field is set equal to or larger than the Z-component $z0$, both of Z-components $z2$, $z3$ in the intensity m1 of the Z-axis gradient magnetic field correspond to one Z-component z1 in the temporary distortion correction table.

Thus, the distortion correction table generating unit 63 partly corrects the temporary distortion correction table. More specifically, if a plurality of Z-components in the reconstruction FOV in the intensities of the actual Z-axis gradient magnetic field correspond to one Z-component in the display FOV in the intensities of the virtual Z-axis gradient magnetic field, the distortion correction table generating unit 63 has a function for generating a distortion correction table for causing only the Z-component which is nearest from the center of the magnetic field of the plurality of Z-components to correspond thereto.

Figure 4:
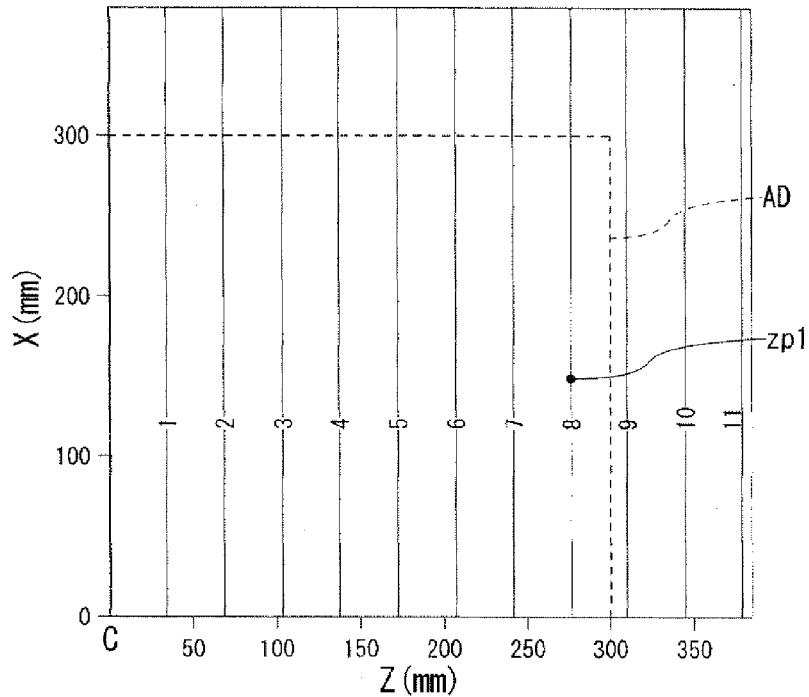
FIG. 4 is a distribution view schematically showing an example of the intensities of a virtual Z-axis gradient magnetic field in an X-Z section.
Figure 5:
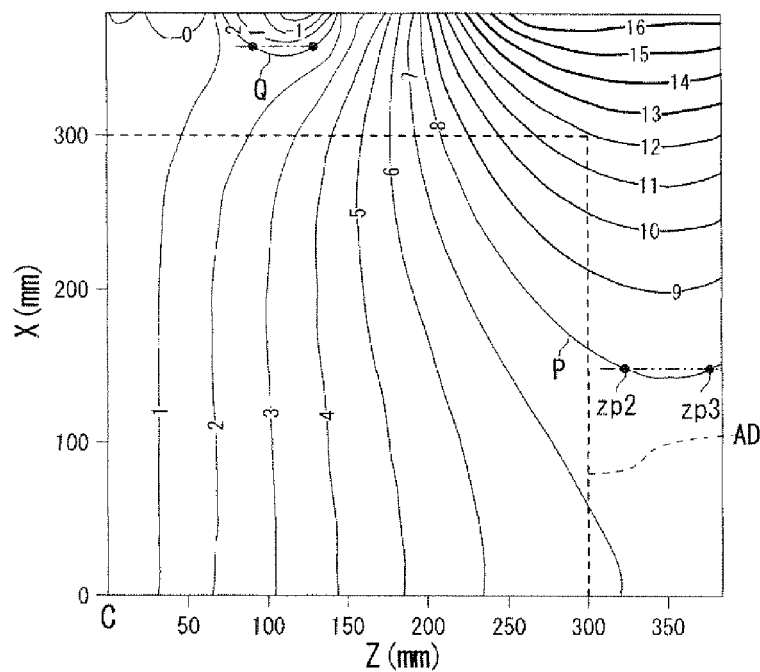
FIG. 5 is a distribution view schematically showing an example of the intensities of an actual Z-axis gradient magnetic field in the X-Z section.

FIG. 4 is a distribution view schematically showing an example of the intensities of the virtual Z-axis gradient magnetic field in an X-Z section. FIG. 5 is a distribution view schematically showing an example of the intensities of the actual Z-axis gradient magnetic field in the X-Z section.

FIGS. 4 and 5 show the X-Z sections (¼ of the bore diameter) of the distribution of the intensities of the Z-axis gradient magnetic field in a required Y-component. Further, the Gz gradient intensities for the range AD (for example, 600 mm×600 mm in Z-direction) of the display FOV are shown in each of FIGS. 4 and 5.

As shown in FIG. 5, a part of the distribution curve of the intensities of the actual Z-axis gradient magnetic field formed by the Z-axis gradient coil 23z has the two-value function (for example, curves P, Q shown in FIG. 5). If the Z-axis gradient magnetic field is generated, a part of the curve P is formed externally of the display FOV in the Z-direction. If the Z-axis gradient magnetic field is generated, the curve Q is formed externally of the display FOV in the X-direction.

Figure 6:
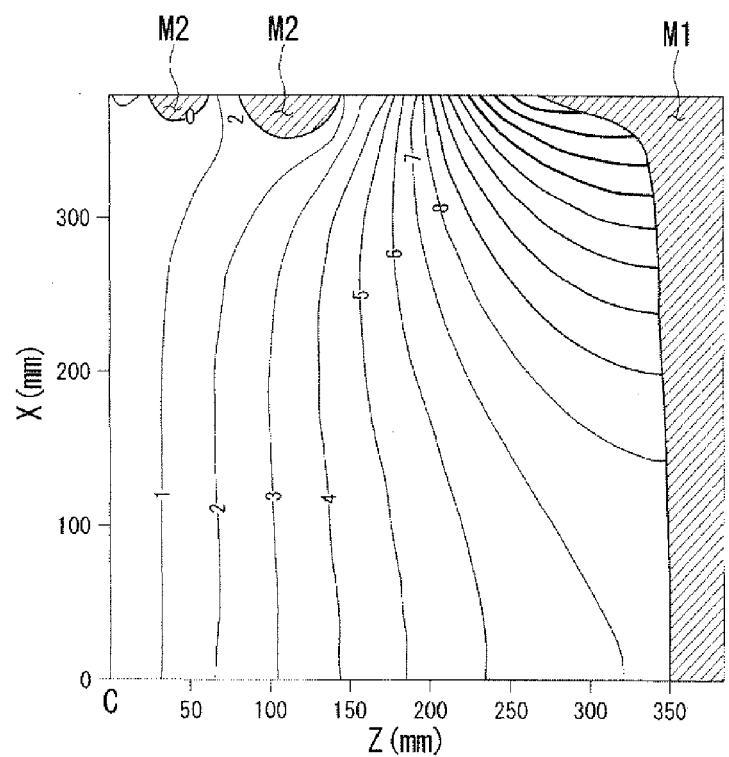
FIG. 6 is a distribution view schematically showing the Z-component groups which migrate to an arbitrary Z-component included in a position coordinate externally of a display reconstruction FOV in the X-Z section.

According to the distortion correction table generated by the distortion correction table generating unit 63, for example, a Z-component included in a position coordinate X=140, Z=zp1 on 8 mT in the display FOV in the distribution of the intensities of the virtual Z-axis gradient magnetic field shown in FIG. 4 correspond only to a Z-component included in a position coordinate X=140, Z=zp2 on the curve P (8 mT) in the display FOV in the intensities of the actual Z-axis gradient magnetic field shown in FIG. 5. More specifically, the distortion correction table is arranged such that only the Z-component included in the position coordinate X=140, Z=zp2 on 8 mT shown in FIG. 5 migrate to the Z-component included in the position coordinate X=140, Z=zp1 on 8 mT shown in FIG. 4. Note that the distortion correction table is arranged such that a Z-component included in a position coordinate X=140, Z=zp3 on 8 mT shown in FIG. 5 migrate to an arbitrary Z-component (for example, included in a position coordinate X=140, Z=1000) externally of the display FOV. FIG. 6 shows a Z-component group (first area M1), shown in FIG. 5 and formed externally of the display FOV in the Z-direction if the Z-axis gradient magnetic field is generated, which migrates to arbitrary Z-component included in the position coordinate externally of the display FOV.

Further, the distortion correction table is arranged such that the respective Z-components included in position coordinates on the curve Q (2 mT) shown in FIG. 5 migrate to the arbitrary Z-component included in the position coordinate externally of the display FOV. FIG. 6 shows Z-component groups (second area M2), shown in FIG. 5 and formed externally of the display FOV in the X-direction if the Z-axis gradient magnetic field is generated, which migrate to the arbitrary Z-component included in the position coordinate externally of the display FOV.

Note that in a state that the static field generation magnet 21 is composed of an iron core normal conducting magnet and the like to which no power is supplied, and of a superconducting magnet to which power is not yet supplied, the distribution of the intensities of the Z-axis gradient magnetic field is obtained by measuring the magnetic field formed only by the Z-axis gradient magnetic field using a magnetic field measuring instrument (magnet sensor). In contrast, in a state that the static field generation magnet 21 is composed of the superconducting magnet and the like to which power is supplied or to which power is supplied once, the distribution of the intensities of a static magnetic field and the distribution of the intensities of the Z-axis gradient magnetic field are obtained by measuring the magnetic fields formed by a static magnetic field and the Z-axis gradient magnetic field using the magnetic field measuring instrument. Further, in the former case, the distribution of the intensities of the static magnetic field may be obtained independently of the distribution of the intensities of the Z-axis gradient magnetic field.

Further, although the distribution of the intensities of the gradient magnetic field may be measured using the magnetic field measuring instrument to obtain it, the distribution of the intensities of the gradient magnetic field may be determined from coil patterns of the gradient coils 23x, 23y, 23z by analyzing them and the determined distribution of the intensities of the gradient magnetic field may be stored to the storage device.

Figure 7:
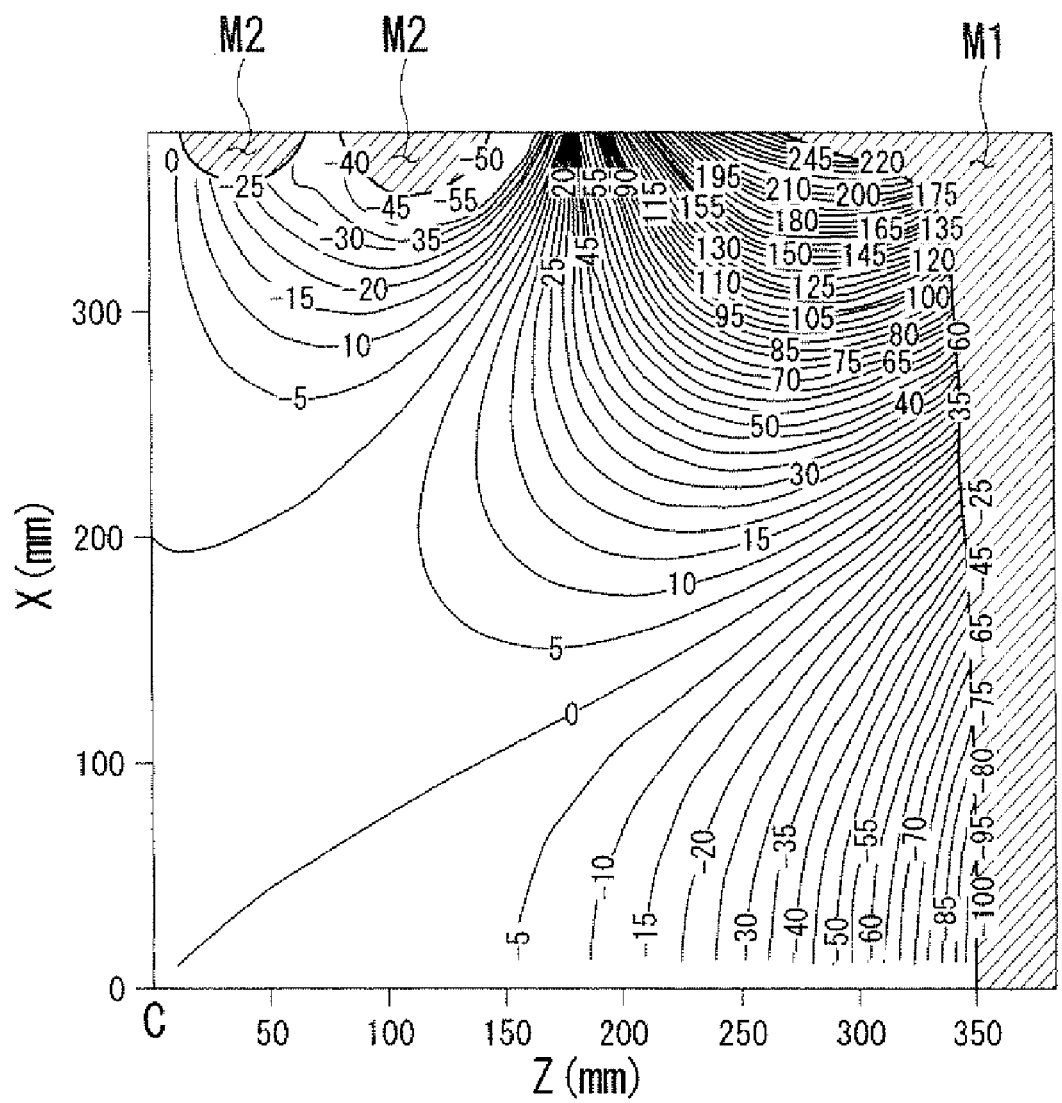
FIG. 7 is a distribution view schematically showing an example of a distortion correction table in the X-Z section shown in FIG. 5.

FIG. 7 is a distribution view schematically showing an example of the distortion correction table in the X-Z section shown in FIG. 5.

A distortion correction table as shown in FIG. 7 is arranged such that it migrates the respective Z-components included in the position coordinates in the first and second areas M1, M2 in the intensities of the actual Z-axis gradient magnetic field to a Z-component (for example, 1000 mm) included in the position coordinate externally of the display FOV.

As described above, the distortion correction table generating unit 63 shown in FIG. 2 generates a two-dimensional distortion correction table as shown in FIG. 7 based on the distribution of the intensities of the magnetic field which is measured based on the magnetic field formed only by the Z-axis gradient coil 23z, and based on the distributions of the intensities of the magnetic fields which are measured based on the magnetic fields formed by the static field generation magnet 21 and the Z-axis gradient coil 23z. Then, the distortion correction table generating unit 63 generates a distortion correction table having a three-dimensional coordinate system by generating a plurality of the two-dimensional distortion correction tables as shown in FIG. 7 along the Y-direction. Further, as to the gradient magnetic fields formed by the X- and Y-axis gradient magnetic fields, distortion correction tables each having a three-dimensional coordinate system can be generated likewise the generation of the distortion correction table of the Z-axis gradient magnetic field formed by the Z-axis gradient coil 23z.

The distortion correction table managing unit 64 has a function for recording the distortion correction table generated by the distortion correction table generating unit 63 to the storage device such as the HD 53 and the like, for obtaining the distortion correction table, which corresponds to a reconstruction section, from the storage device in response to a request from the image correcting unit 65, and for outputting the corrected position coordinates corresponding to the respective position coordinates [X, Y, Z] in the display FOV to the image correcting unit 65.

The image correcting unit 65 has a function for correcting the reconstructed image by requesting the distortion correction table managing unit 64 to obtain the corrected position coordinates corresponding to the respective position coordinates [X, Y, Z] in the reconstruction FOV from the storage device and applying them to the respective position coordinates constituting the reconstructed image generated by the image generating unit 62. A corrected image is displayed as a diagnostic image through the display device 55. Further, the data of the corrected image is stored to an image database (not shown).

Figure 9:
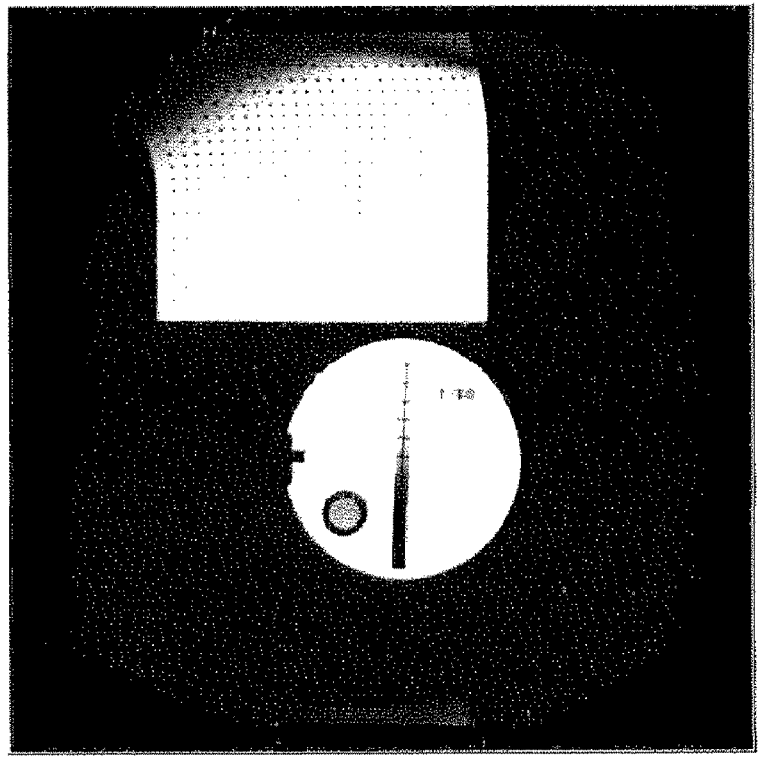
FIG. 9 is a view showing the reconstructed image in the X-Y section after it is corrected by the MRI apparatus of the embodiment.
Figure 8:
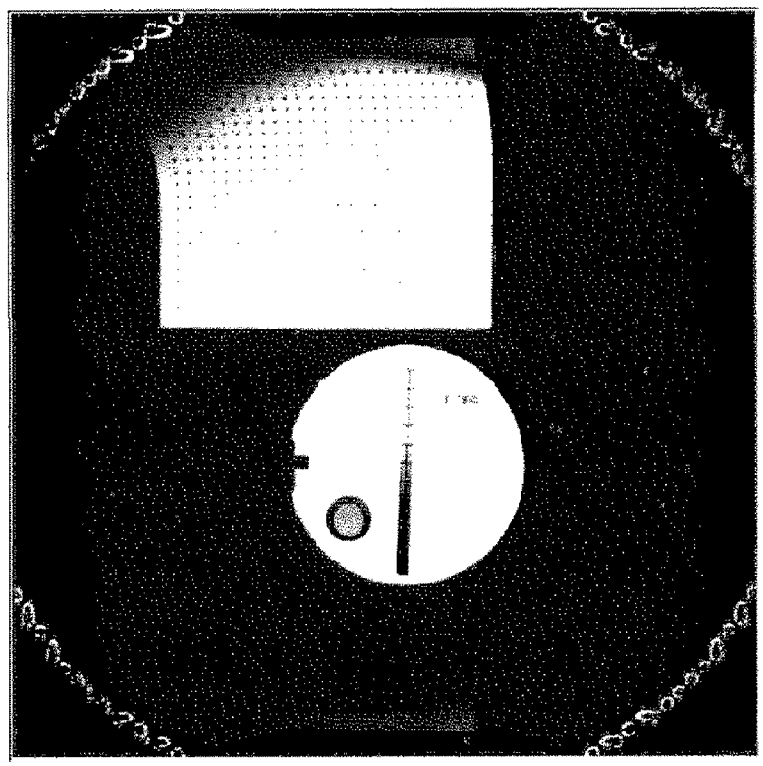
FIG. 8 is a view showing a reconstructed image in an X-Y section formed by a conventional MRI apparatus.

FIG. 8 is a view showing the reconstructed image in an X-Y section formed by a conventional MRI apparatus, and FIG. 9 is a view showing the reconstructed image in the X-Y section after it is corrected by the MRI apparatus of the embodiment.

If the image shown in FIG. 9 is compared with the image shown in FIG. 8, it can be found that an artifact, which is caused by that the Z-component included in the position coordinate in the display FOV in the distribution of the intensities of the virtual Z-axis gradient magnetic field corresponds to the respective Z-components included in a plurality of position coordinates in the reconstruction FOV in the distribution of the intensities of the actual Z-axis gradient magnetic field, is removed from the image shown in FIG. 9.

According to the MRI apparatus of the embodiment 10, even if a relatively wide display FOV is set, a good diagnostic image from which an artifact is removed can be generated and displayed.

What is claimed is:

1. A magnetic resonance imaging apparatus comprising:
a static field generation magnet configured to generate a static magnetic field;
a gradient coil configured to apply gradient magnetic fields superimposed on the static magnetic field to an object;
an RF coil configured to receive a magnetic resonance signal generated by the object;
an image reconstructing unit configured to generate a reconstructed image in a reconstruction field of view (FOV) of the object based on the magnetic resonance signal;
a correction data storage unit configured to store correction data of a position coordinate, in which the position coordinate in the reconstruction FOV is caused to correspond to a position coordinate in a display FOV included in a reconstruction FOV based on an intensity of the gradient magnetic field at a corresponding position,
wherein if both of a first position coordinate and a second position coordinate in the reconstruction FOV correspond to one position coordinate in the display FOV, the correction data for the corresponding position coordinate in the display FOV is based on only the one of the first and second position coordinates that is located closest to a center of the reconstruction FOV; and
an image processing unit configured to correct the reconstructed image based on the stored correction data, and to obtain an image of the display FOV.

2. The magnetic resonance imaging apparatus according to claim 1, wherein the first position coordinate and the second position coordinate have the same intensity of gradient magnetic field.

3. The magnetic resonance imaging apparatus according to claim 1, wherein the first position coordinate and the second position coordinate have the same intensity of gradient magnetic field which is represented by a function having equal values at said first and second position coordinates.

4. The magnetic resonance imaging apparatus according to claim 1, wherein the correction data storage device stores the correction data for a position coordinate external to the display FOV.

5. The magnetic resonance imaging apparatus according to claim 1, wherein the correction data storage device stores the correction data for a three-dimensional space.

6. A magnetic resonance imaging method comprising:
receiving a magnetic resonance signal generated from an object subjected to a gradient magnetic field superimposed on a static magnetic field;
generating a reconstructed image in a reconstruction field of view (FOV) of the object based on the received magnetic resonance signal;
correcting the reconstructed image based on correction data of a position coordinate, in which the position coordinate in the reconstruction FOV is caused to correspond to a position coordinate in a display FOV included in the reconstruction FOV based on an intensity of the gradient magnetic field at a corresponding position wherein, if both a first position coordinate and a second position coordinate in the reconstruction FOV correspond to a single position coordinate in the display FOV, then only the one of the first and second position coordinate that is closest to the center of the reconstruction FOV is used for correction data corresponding to said single position coordinate in the display FOV, and
obtaining a corrected image of the display FOV.

7. A magnetic resonance imaging apparatus comprising:
a static field generation magnet configured to generate a static magnetic field;
a gradient coil configured to apply gradient magnetic fields superimposed on the static magnetic field to an object;
an RF coil configured to receive a magnetic resonance signal generated by the object from an imaging volume;
an image reconstructing unit configured to generate a reconstructed image in a reconstruction field of view (FOV) of the object based on the received magnetic resonance signal;
a correction data storage unit configured to store correction data of a position coordinate, in which a position coordinate in the reconstruction FOV is caused to correspond to a position coordinate in a display FOV based on an intensity of the gradient magnetic field at a corresponding spatial position in the imaging volume;
an image processing unit configured to correct the reconstructed image based on the correction data, and to obtain an image of the display FOV; and
wherein, if said reconstruction FOV is sufficiently large to encompass at least some equal-value intensities of gradient magnetic field at two points spaced at different distances from a center of the reconstruction FOV, then said stored correction data for a given point in the reconstruction FOV having equal-valued gradient magnetic field intensities is based on the point spaced closest to the center of the reconstruction FOV.

* * * * *